(12) United States Patent
Arrazolo

(10) Patent No.: US 11,540,910 B2
(45) Date of Patent: Jan. 3, 2023

(54) DOUBLE BARRELED INJECTOR ASSEMBLY

(71) Applicant: Juan Arrazolo, Mankato, MN (US)

(72) Inventor: Juan Arrazolo, Mankato, MN (US)

(*) Notice: Subject to any disclaimer, the term of this patent is extended or adjusted under 35 U.S.C. 154(b) by 408 days.

(21) Appl. No.: 16/842,851

(22) Filed: Apr. 8, 2020

(65) Prior Publication Data
US 2021/0315677 A1  Oct. 14, 2021

(51) Int. Cl.
*A61D 7/00* (2006.01)
*A61M 5/19* (2006.01)
*A61M 5/34* (2006.01)
*A61M 5/20* (2006.01)
*A61M 5/315* (2006.01)
*A61M 5/31* (2006.01)

(52) U.S. Cl.
CPC .............. *A61D 7/00* (2013.01); *A61M 5/19* (2013.01); *A61M 5/2033* (2013.01); *A61M 5/31596* (2013.01); *A61M 5/34* (2013.01); *A61M 2005/3114* (2013.01); *A61M 2202/30* (2013.01); *A61M 2250/00* (2013.01)

(58) Field of Classification Search
CPC ...... A61M 5/31596; A61M 2005/3114; A61M 5/19
See application file for complete search history.

(56) References Cited

U.S. PATENT DOCUMENTS

| | | | |
|---|---|---|---|
| 3,467,096 A | 9/1969 | Horn | |
| 4,673,395 A * | 6/1987 | Phillips | A61M 5/31581 604/191 |
| 5,049,135 A * | 9/1991 | Davis | A61M 1/0062 604/218 |
| 5,520,658 A | 5/1996 | Holm | |
| 5,542,934 A * | 8/1996 | Silver | A61M 5/19 604/232 |
| 5,759,171 A | 6/1998 | Coelho | |
| 6,827,701 B2 | 12/2004 | MacMahon | |
| 7,959,612 B2 | 6/2011 | Thompson | |
| 8,337,450 B2 | 12/2012 | Fojtik | |
| D829,888 S | 10/2018 | Xie | |
| 2014/0257179 A1* | 9/2014 | Schwab | A61M 5/31596 604/82 |

FOREIGN PATENT DOCUMENTS

WO  WO2009131773  10/2009

* cited by examiner

*Primary Examiner* — Bradley J Osinski
(74) *Attorney, Agent, or Firm* — Kaufhold & Dix; Bradley Osins Kaufhold

(57) ABSTRACT

A double barreled injector assembly for performing multiple sequential vaccinations includes a pair of barrels, each of which is engaged by a first terminus thereof to a bar and extends from a lower face thereof. A respective agent can be positioned in each barrel. Each barrel has an orifice positioned in a second terminus thereof. A pair of actuators is engaged to an upper face of the bar. Each actuator is operationally engaged to a respective barrel and can be actuated by action of a hand of a user to dispense an associated agent through the orifice of the respective barrel into an animal. The injector assembly allows the user to perform multiple sequential vaccinations with two different vaccines and will be useful in vaccination of herds or flocks of livestock, such as poultry, cattle, and the like.

14 Claims, 4 Drawing Sheets

DOUBLE BARRELED INJECTOR ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention

The disclosure relates to injector assemblies and more particularly pertains to a new injector assembly for performing multiple sequential vaccinations.

(2) Description of Related Art Including Information Disclosed Under 37 CFR 1.97 and 1.98

The prior art relates to injector assemblies. Prior art injector assemblies may comprise a device for connecting two hypodermic syringes by their barrels, as well as devices that have two barrels for simultaneous dispensing.

BRIEF SUMMARY OF THE INVENTION

An embodiment of the disclosure meets the needs presented above by generally comprising a pair of barrels, each of which is engaged by a first terminus thereof to a bar and extends from a lower face thereof. Each barrel is configured to position a respective agent and has an orifice positioned in a second terminus thereof. A pair of actuators is engaged to an upper face of the bar. Each actuator is operationally engaged to a respective barrel and is configured to be actuated by action of a hand of a user to dispense an associated agent through the orifice of the respective barrel into an animal. The injector assembly allows the user to perform multiple sequential vaccinations with two different vaccines and will be useful in vaccination of herds or flocks of livestock, such as poultry, cattle, and the like.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein.

DETAILED DESCRIPTION OF THE INVENTION

Figure 1:
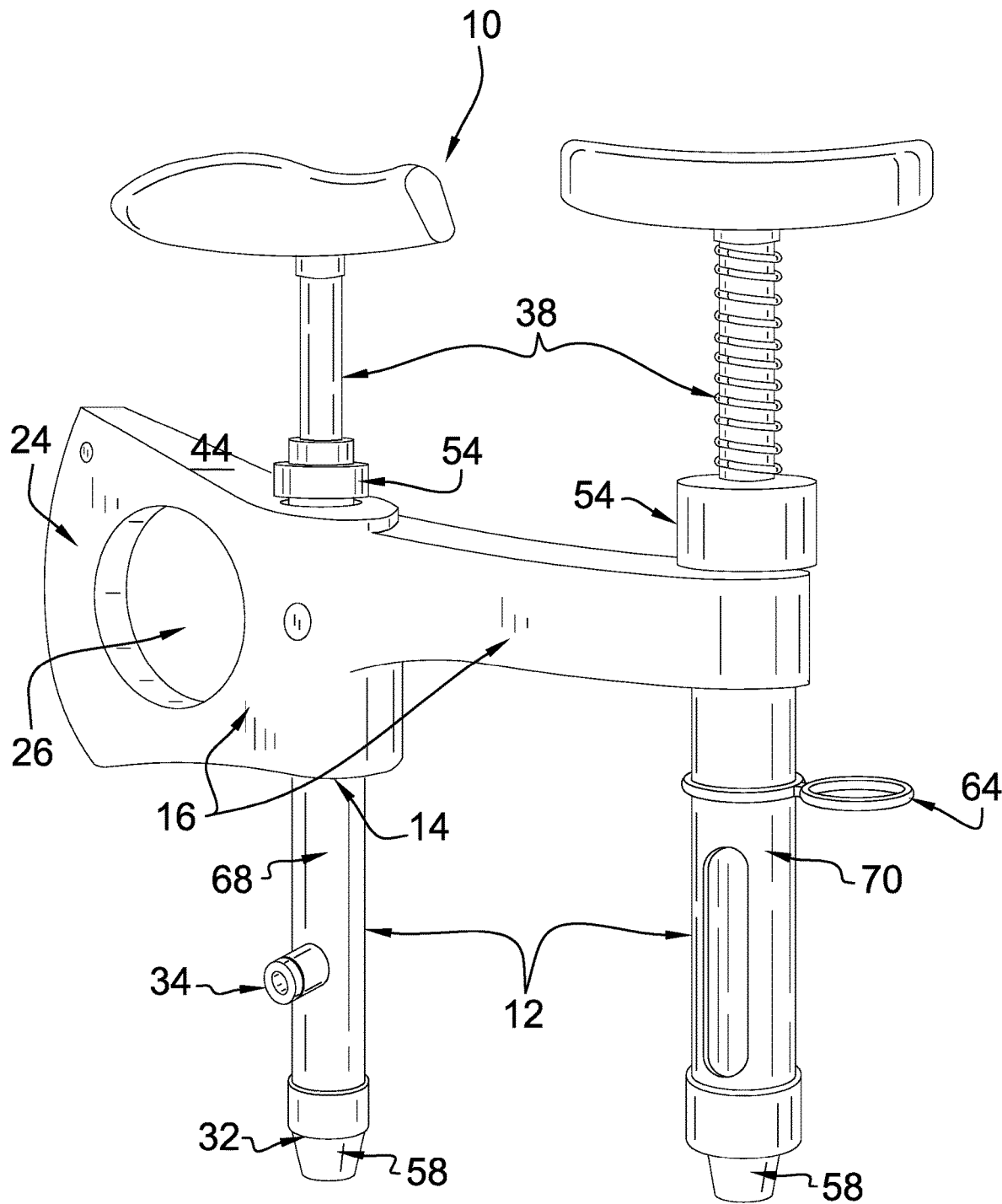
FIG. 1 is an isometric perspective view of a double barreled injector assembly according to an embodiment of the disclosure.

With reference now to the drawings, and in particular to FIGS. 1 through 5 thereof, a new injector assembly embodying the principles and concepts of an embodiment of the disclosure and generally designated by the reference numeral 10 will be described.

As best illustrated in FIGS. 1 through 5, the double barreled injector assembly 10 generally comprises a pair of barrels 12, each of which is engaged by a first terminus 14 thereof to a bar 16 and extends from a lower face 18 thereof. The bar 16 comprises a first section 20 and a second section 22. The first section 20 is substantially rectangularly shaped when viewed from a side 24 of the bar 16. The first section 20 has a cutout 26 positioned therethrough, which is circular and configured for insertion of a digit of a hand of a user. The second section 22 extends coplanarly from a corner 28 of the first section 20. The second section 22 is both dimensionally shorter and dimensionally wider than the first section 20.

Each barrel 12 is configured to position a respective agent, such as, but not limited to, a solution or suspension of a vaccine, a hormone, or the like. Each barrel 12 has an orifice 30 positioned in a second terminus 32 thereof. The barrels 12 are substantially parallel. One of the barrels 12 is engaged to the second section 22 distal from the first section 20, while the other of the barrels 12 is engaged to the first section 20 proximate to the second section 22.

Figure 2:
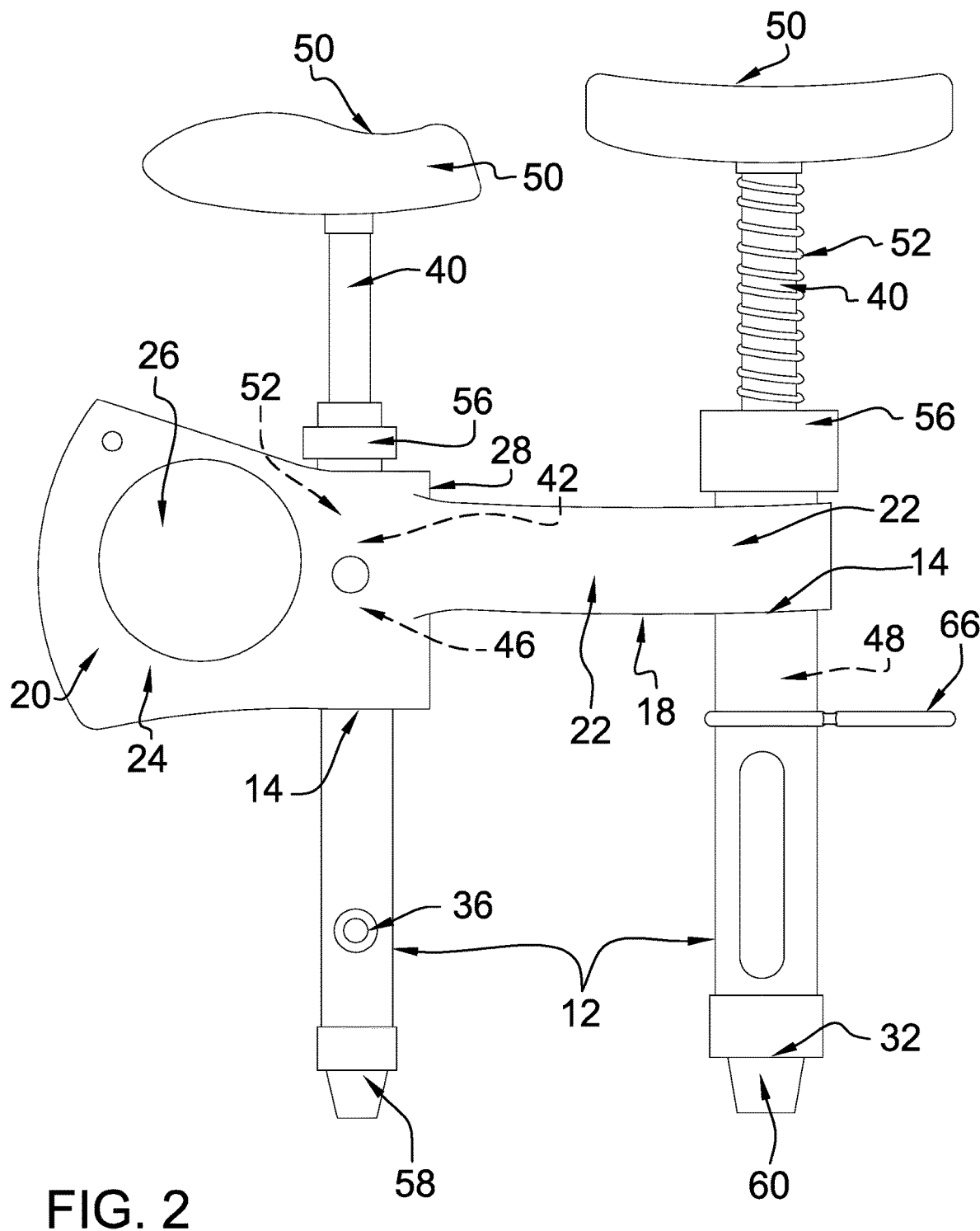
FIG. 2 is a side view of an embodiment of the disclosure.

At least one of the barrels 12 may have a refill connector 34 engaged thereto and configured to selectively engage at least one of a bottle and a tube. The at least one of the barrels 12 thus is configured for sequential filling with a respective agent. The refill connector 34 may comprise a tube connector 36, as shown in FIG. 2, although the present invention also anticipates the refill connector 34 comprising a bottle connector (not shown). The tube connector 36 is configured to engage a tube leading to a bottle that contains the respective agent so that the respective agent can flow to the at least one of the barrels 12. Thus, a variety of configurations for the assembly 10 are anticipated by this invention: an assembly 10 devoid of a refill connector 34, an assembly 10 having one refill connector 34, and an assembly 10 having two refill connectors 34.

A pair of actuators 38 is engaged to an upper face 44 of the bar 16. Each actuator 38 is operationally engaged to a respective barrel 12. The actuator 38 is configured to be actuated by action of a hand of a user to dispense an associated agent through the orifice 30 of the respective barrel 12 into an animal. The injector assembly 10 allows the user to perform multiple sequential vaccinations with two different vaccines and will be useful in vaccinating of herds or flocks of livestock, such as poultry, cattle, and the like. The present invention also anticipates the assembly 10 being used for injection of hormones, antibiotics, and the like.

The actuator 38 may comprise a rod 40, which extends through a respective channel 42 that is positioned through the bar 16. The rod 40 is slidably engaged to the bar 16 and protrudes from the upper face 44. The rod 40 is operationally engaged to at least one of a piston 46 and a disc 48. The at least one of a piston 46 and a disc 48 is positioned to sealably engage the respective barrel 12 and to slide within the respective barrel 12 to dispense the associated agent through the orifice 30 of the respective barrel 12 into the animal.

A handle 50 is coupled to the rod 40 distal from the bar 16. A spring 52 is operationally engaged to the bar 16 and the rod 40 and thus is positioned to be tensioned as the handle 50 is depressed toward the bar 16 to dispense the associated agent. The spring 52 is positioned to rebound upon release of the handle 50 so that the rod 40 defaults to an extended position, wherein the rod 40 protrudes from the upper face 44 of the bar 16. The spring 52 is positioned at least one of within the channel 42, as shown in FIG. 2, left, and externally from the bar 16 around the rod 40, as shown in FIG. 2, right. The present invention also anticipates the actuator 38 being of other types, for example, mechanical and electromechanical linear actuators.

The actuator 38 has an adjuster 54 operationally engaged thereto, which is configured to adjust a volume of the associated agent that is to be dispensed through the orifice 30. The adjuster 54 may comprise a ring 56, which is positioned around the rod 40 adjacent to the upper face 44 of the bar 16. The ring 56 is configured to be turned to adjust a length of travel of the rod 40 into the barrel 12. The present invention also anticipates the adjuster 54 comprising other adjusting means, such as, but not limited to, using pistons 46 of a variety of sizes.

Figures 3, 4:
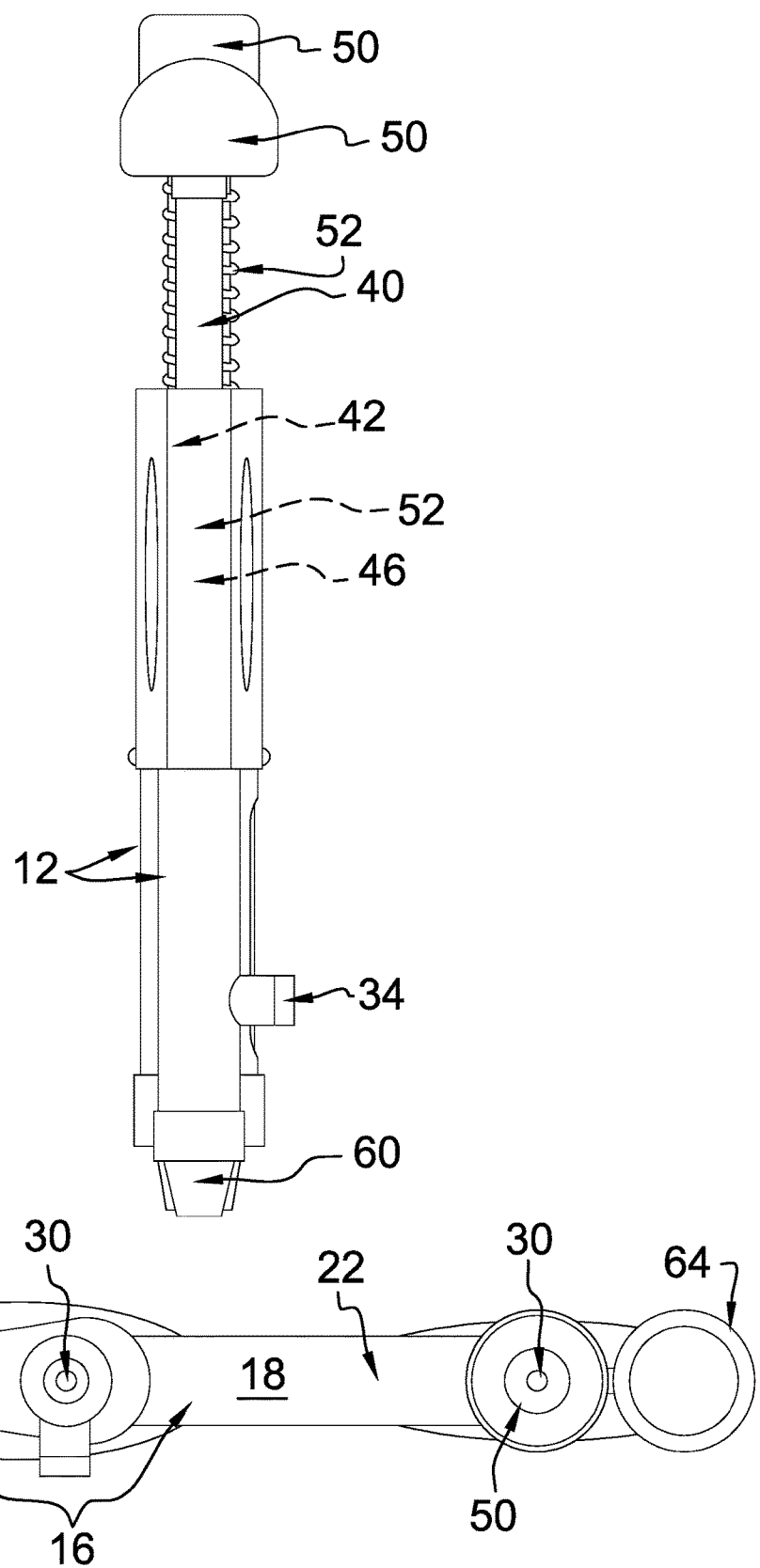
FIG. 3 is an end view of an embodiment of the disclosure.
FIG. 4 is a bottom view of an embodiment of the disclosure.

Each barrel 12 has a needle connector 58 engaged to the second terminus 32 thereof. The needle connector 58 is configured to engage a respective needle and may comprise a male Luer tip 60, as shown in FIG. 4.

Figure 5:
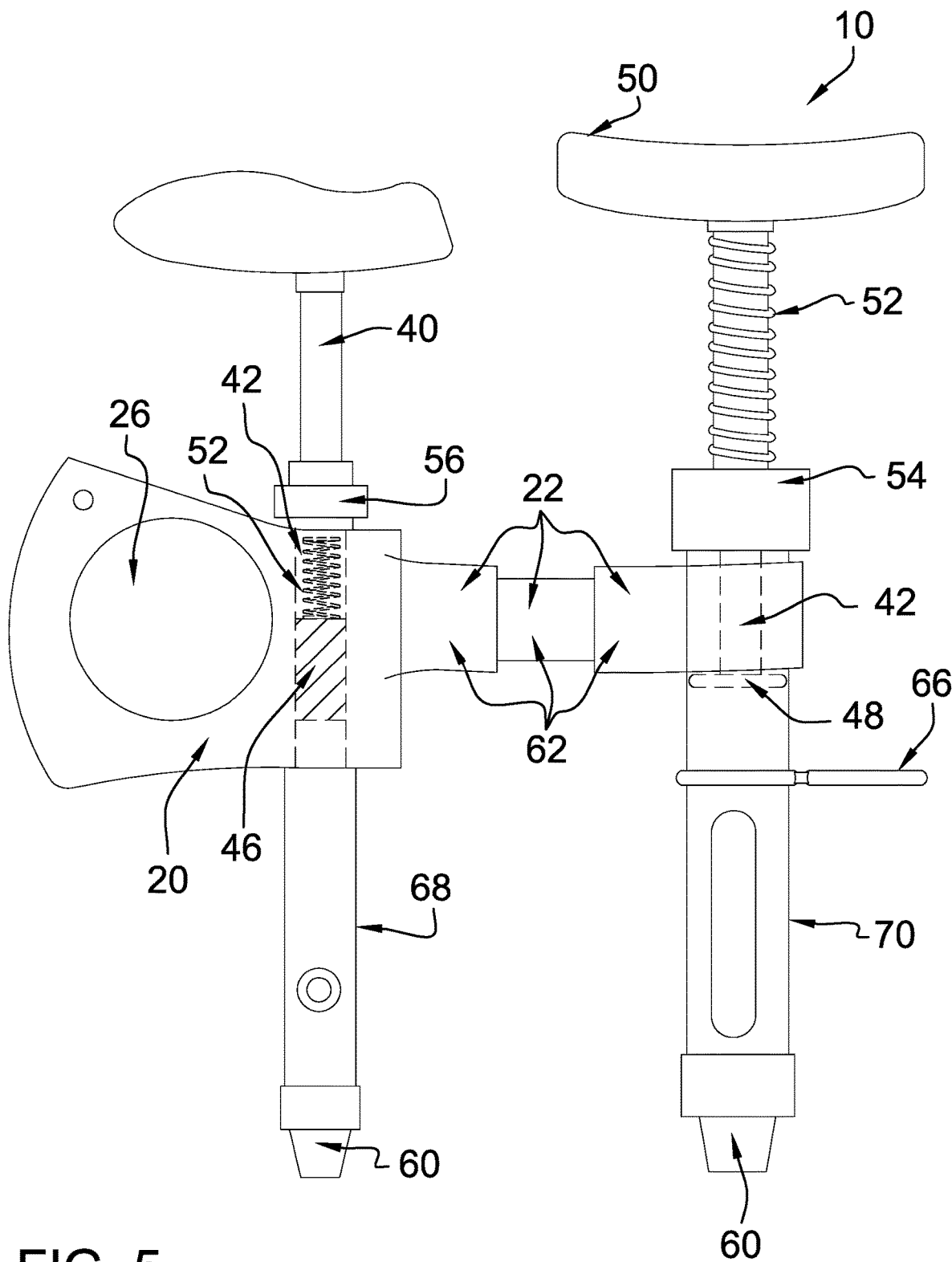
FIG. 5 is a side view of an alternative embodiment of the disclosure.

The present invention anticipates the second section 22 of the bar 16 being tubular and comprising a plurality of nested segments 62, as shown in FIG. 5. As such, the barrels 12 and actuators 38 can be selectively distanced to fit the hand of the user. The present invention also anticipates one of the nested section 62 being selectively engageable to another of the nested sections 62, or to the first section 20 of the bar 16. As such, different types of barrels 12 and associated actuators 38 can be selectively combined.

A fastener 64 may be engaged to one of the barrels 12 and configured to engage the tube leading to the bottle. The fastener 64 stabilizes the tube relative to the tube connector 36. The fastener 64 may comprise a loop 66, which is engaged to and which extends from the one of the barrels 12. The loop 66 is configured to insert the tube leading to the bottle.

In one example of use for the embodiment shown in FIGS. 1-4, a solution of a first vaccine is fed from a bottle through the tube into a first barrel 68 having the tube connector 36 engaged thereto. A second vaccine is drawn into a second barrel 70 by depressing the handle 50, positioning an attached needle into a solution of the second vaccine, and then releasing the handle 50 so that the solution of the second vaccine is drawn into the second barrel 70. The first vaccine can be injected into one body part of the animal by depressing the handle 50 associated with the first barrel 68, while the second vaccine can be injected into a second body part of the animal by depressing the handle 50 associated with the second barrel 70. Prior to releasing the handle 50 associated with the second barrel 70, the attached needle is again positioned in the solution of the second vaccine. The first vaccine automatically flows to refill the first barrel 68, and the user is positioned to vaccinate another animal.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the elements is present, unless the context clearly requires that there be only one of the elements.

I claim:

1. A double barreled injector assembly comprising:
    a bar;
    a pair of barrels each engaged by a first terminus thereof to the bar and extending from a lower face thereof, each barrel being configured for positioning a respective agent, each barrel having an orifice positioned in a second terminus thereof;
    a pair of actuators engaged to an upper face of the bar, each actuator being operationally engaged to a respective barrel of the pair of barrels, wherein each actuator is configured for being actuated by action of a hand of a user for dispensing an associated agent through the orifice of the respective barrel of the pair of barrels into an animal; and
    wherein the bar comprises:
        a first section the first section being substantially rectangularly shaped when viewed from a side of the bar, the first section having a cutout positioned therethrough, wherein the cutout is configured for insertion of a digit of the hand of the user; and
        a second section, the second section extending coplanarly from a corner of the first section, the second section being dimensionally shorter and dimensionally wider than the first section.

2. The double barreled injector assembly of claim 1, wherein the cutout is circular.

3. The double barreled injector assembly of claim 1, wherein the barrels are substantially parallel.

4. The double barreled injector assembly of claim 1, wherein at least one of the barrels has a refill connector engaged thereto and being configured for selectively engaging at least one of a bottle and a tube, wherein the at least one of the barrels is configured for sequential filling with a respective agent.

5. The double barreled injector assembly of claim 2, wherein the refill connector comprises a tube connector, wherein the tube connector is configured for engaging the tube leading to the bottle containing the respective agent, such that the respective agent can flow to the at least one of the barrels.

6. The double barreled injector assembly of claim 5, further including a fastener engaged to one of the barrels and being configured for engaging the tube leading to the bottle for stabilizing the tube relative to the tube connector.

7. The double barreled injector assembly of claim 6, wherein the fastener comprises a loop engaged to and extending from the one of the barrels, wherein the loop is configured for inserting the tube leading to the bottle.

8. The double barreled injector assembly of claim 1, wherein:
one of the barrels is engaged to the second section distal from the first section; and
the other of the barrels is engaged to the first section proximate to the second section.

9. The double barreled injector assembly of claim 1, wherein each actuator comprises:
a rod extending through a respective channel positioned through the bar, such that the rod is slidably engaged to the bar, and such that the rod protrudes from the upper face, the rod being operationally engaged to at least one of a piston and a disc, the at least one of a piston and a disc being positioned for sealably engaging the respective barrel and for sliding within the respective barrel for dispensing the associated agent through the orifice of the respective barrel into the animal;
a handle coupled to the rod distal from the bar; and
a spring operationally engaged to the bar and the rod, such that the spring is positioned for tensioning as the handle is depressed toward the bar, and for rebounding upon release of the handle, such that the rod defaults to an extended position wherein the rod protrudes from the upper face of the bar, the spring being positioned at least one of within the channel and externally from the bar around the rod.

10. The double barreled injector assembly of claim 9, further including the actuator having an adjuster operationally engaged thereto and being configured for adjusting a volume of the associated agent to be dispensed through the orifice positioned in the second terminus of the respective barrel.

11. The double barreled injector assembly of claim 10, wherein the adjuster comprises a ring positioned around the rod adjacent to the upper face of the bar, wherein the ring is configured for turning to adjust a length of travel of the rod into the barrel.

12. The double barreled injector assembly of claim 1, wherein each barrel has a needle connector engaged to the second terminus thereof and being configured to engage a respective needle.

13. The double barreled injector assembly of claim 12, wherein the needle connector comprising a male Luer tip.

14. A double barreled injector assembly comprising:
a bar, the bar comprising a first section and a second section, the first section being substantially rectangularly shaped when viewed from a side of the bar, the first section having a cutout positioned therethrough, wherein the cutout is configured for insertion of a digit of a hand of a user, the second section extending coplanarly from a corner of the first section, the second section being dimensionally shorter and dimensionally wider than the first section, the cutout being circular;
a pair of barrels each engaged by a first terminus thereof to the bar and extending from a lower face thereof, each barrel being configured for positioning a respective agent, each barrel having an orifice positioned in a second terminus thereof, the barrels being substantially parallel, at least one of the barrels having a refill connector engaged thereto and being configured for selectively engaging at least one of a bottle and a tube, wherein the at least one of the barrels is configured for sequential filling with a respective agent, the refill connector comprising a tube connector, wherein the tube connector is configured for engaging a tube leading to a bottle containing the respective agent, such that the respective agent can flow to the at least one of the barrels, one of the barrels being engaged to the second section distal from the first section, the other of the barrels being engaged to the first section proximate to the second section;
a pair of actuators engaged to an upper face of the bar, each actuator being operationally engaged to a respective barrel of the pair of barrels, wherein each actuator is configured for being actuated by action of the hand of the user for dispensing an associated agent through the orifice of the respective barrel of the pair of barrels into an animal, each actuator comprising:
a rod extending through a respective channel positioned through the bar, such that the rod is slidably engaged to the bar, and such that the rod protrudes from the upper face, the rod being operationally engaged to at least one of a piston and a disc, the at least one of a piston and a disc being positioned for sealably engaging the respective barrel and for sliding within the respective barrel for dispensing the associated agent through the orifice of the respective barrel into the animal,
a handle coupled to the rod distal from the bar, and
a spring operationally engaged to the bar and the rod, such that the spring is positioned for tensioning as the handle is depressed toward the bar, and for rebounding upon release of the handle, such that the rod defaults to an extended position wherein the rod protrudes from the upper face of the bar, the spring being positioned at least one of within the channel and externally from the bar around the rod;
each barrel having a needle connector engaged to the second terminus thereof and being configured to engage a respective needle, the needle connector comprising a male Luer tip;
the actuator having an adjuster operationally engaged thereto and being configured for adjusting a volume of the associated agent to be dispensed through the orifice positioned in the second terminus of the respective barrel, the adjuster comprising a ring positioned around the rod adjacent to the upper face of the bar, wherein the ring is configured for turning to adjust a length of travel of the rod into the barrel; and a fastener engaged to one of the barrels and being configured for engaging the tube leading to the bottle for stabilizing the tube relative to the tube connector, the fastener comprising a loop engaged to and extending from the one of the barrels, wherein the loop is configured for inserting the tube leading to the bottle.

* * * * *